United States Patent [19]

Meilland, deceased

[11] Patent Number: Plant 7,718

[45] Date of Patent: Nov. 26, 1991

[54] ROSE PLANT—MEICAUF VARIETY

[75] Inventor: Marie-Louise Meilland, deceased, late of Antibes, France, by Jean-Pierre Le Naour, Legal Representative

[73] Assignee: The Conard-Pyle Company, West Grove, Pa.

[21] Appl. No.: 526,989

[22] Filed: May 22, 1990

[51] Int. Cl.[5] ..... A01H 5/00
[52] U.S. Cl. ..... Plt./20
[58] Field of Search ..... Plt./20, 21

[56] References Cited

U.S. PATENT DOCUMENTS

P.P. 2,598 2/1966 Meilland ..... PLT/21

*Primary Examiner*—Howard J. Locker
*Attorney, Agent, or Firm*—Burns, Doane, Swecker & Mathis

[57] ABSTRACT

A new and distinct variety of Hybrid Tea rose plant is provided which abundantly and continuously forms attractive double blossoms which are turkey red on the upper surface and cardinal red on the under surface. Such blossoms are long lasting. The plant exhibits an erect growth habit, very vigorous vegetation, and is well suited for growing in parks and gardens. Additionally, the plant is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the cross between the Queen Elizabeth variety (U.S. Plant Pat. No. 1,259) by the Karl Herbst variety (nonpatented in the United States) to produce a plant which was crossed by the Meicesar variety (nonpatented in the United States). The male parent (i.e., the pollen parent) was the product of a cross between the Meidanu variety (nonpatented in the United States) by the Meifan variety (nonpatented in the United States). The parentage of the new variety can be summarized as follows:

[Queen Elizabeth × Karl Herbst) × Meicesar]33
(meidanu × Meifan).

The seeds resulting from the above pollination were sown and 68 small plants were obtained which were physically and biologically different from each other. Selective study resulted in the identification of a single plant of the new variety.

It was found that the new variety of Hybrid Tea rose plant of the present invention possesses the following combination of characteristics:

(a) forms continuously and in abundance attractive long lasting double blossoms which are turkey red on the upper surface and cardinal red on the under surface,
(b) exhibits an erect growth habit,
(c) exhibits very vigorous vegetation,
(d) is particularly suited for growing in parks and gardens, and
(e) is not particularly affected by cryptogamic diseases.

The new variety well meets the needs of the horticultural industry for all uses and is particularly well suited for forming attractive ornamentation when grown outdoors.

The new variety has been found to undergo asexual propagation by a number of routes, including budding, grafting, cuttage, etc. Asexual reproduction by the above mentioned methods as performed in France shows that the characteristics of the new variety are strictly transmissable from one generation to another.

The new variety has been named the Meicauf variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa forebelli* understock and growing outdoors at LeCannet des Maures, Var, France.

Figures 1, 2, 3, 4, 5, 6, 7, 8, 9, 10, 11, 12, 13, 14, 15, 16:
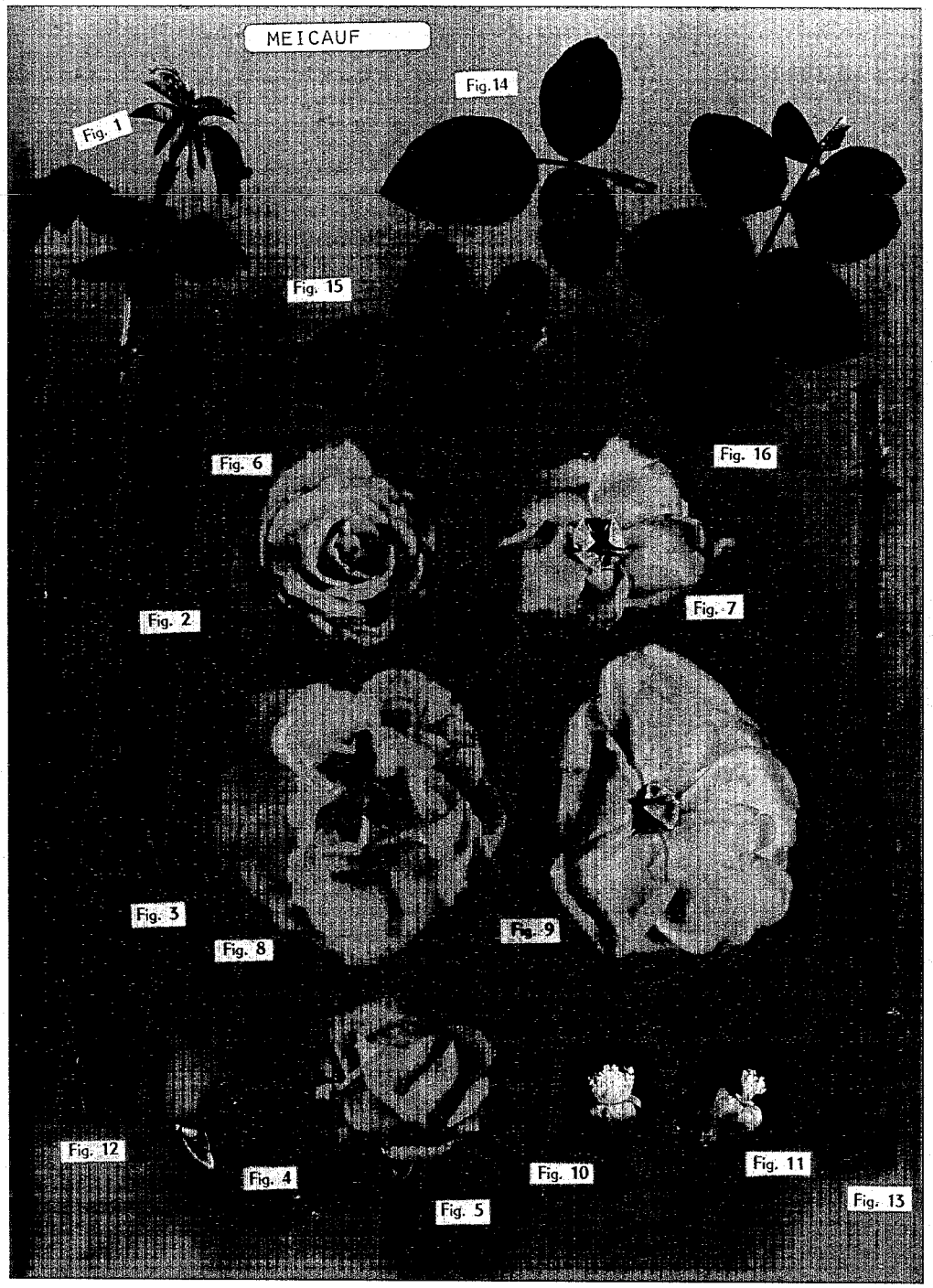
FIG. 1 illustrates a specimen of a young shoot.
FIG. 2 illustrates a specimen of a floral bud before the opening of the sepals.
FIG. 3 illustrates a specimen of a floral bud at the opening of the sepals.

FIG. 4. illustrates a specimen of a floral bud at the opening of the petals;

FIG. 5 illustrates a specimen of a flower in the course of opening;

FIG. 6 illustrates a specimen of a blooming flower —plan view—obverse;

FIG. 7 illustrates a specimen of a blooming flower —plan view—reverse;

FIG. 8 illustrates a specimen of a fully open flower immediately prior to petal drop—plan view—obverse;

FIG. 9 illustrates a specimen of a fully open flower immediately prior to petal drop—plan view—reverse;

FIG. 10 illustrates a specimen of a floral receptacle showing the arrrangement of the stamens and pistils;

FIG. 11 illustrates a specimen of a floral receptacle showing the arrangement of the pistils (stamens removed);

FIG. 12 illustrates a specimen of a flowering stem;

FIG. 13 illustrates a specimen of a main branch;

FIG. 14 illustrates a specimen of a leaf with three leaflets—plan view—upper surface;

FIG. 15 illustrates a specimen of a leaf with five leaflets—plan view—under surface; and FIG. 16 illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of two year old plants made during June while budded on *Rosa froebelli* understock and growing outdoors at le-Cannet des Maures, Var, France. The coloration in common terms precedes reference to the chart.

Class: Hybrid Tea.

Plant:

*Height.*—Approximately 100 to 150 cm.

*Habit.*—Erect.

Branches:

*Color.*—Young stems: light green, yellow-Green Group 146C, more or less suffused with reddish coloration. Adult wood: medium green, Yellow-Green Group 146B.

*Thorns.*—Size: average. Quantity: fairly numerous. Color: reddish on young stems and greenish changing to tan on mature wood.

Leaves:

*Stipules.*—Adnate, pectinate, wide and linear.

*Petioles.*—upper surface: striped reddish brown on young foliage and medium green on adult foliage with more or less glandular edges. Under surface; light green, smooth.

*Leaflets.*—Number: 3, 5, and 7 (most often). Shape: oval. Serration: single and regular. Texture; consistent. General appearance: dense and semi-mat foliage. Color (young foliage): Upper surface: light green, Yellow-Green Group 146C, very widely stained with reddish coloration. Under surface: reddish-brown. Color (adult foliage): Upper surface: dark green, Yellow-Green Group 147A. Under surface: medium green, Yellow-Green Group 147B.

Inflorescence:

*Number of flowers.*—1 to 3 blooms per stem, usually 1 per stem.

*Peduncle.*—Straight, rigid, smooth, medium green in coloration, bears a few glandular acicules. The length is approximately 5.5 to 6 cm. on average.

*Sepals.*—Upper surface: greenish tomentose, widely stained with reddish-brown coloration. Under surface: medium green, more or less stained with reddish-brown coloration, more or less glandular, the edges of the outer sepals are more or less appendiculated.

*Buds.*—Shape: round with an elongated tip. Length: approximately 3 cm. on average. Size: large. Color upon opening: Upper surface: guardsman red, Red Group 45A. Under surface: bright cardinal red, Red Group 53B.

*Flower.*—Shape: cup-like. Diameter: approximately 13 to 14 cm. on average. Color (when opening begins): Upper surface: currant red, Red Group 46B. Under surface: cardinal red, Red Group 53B. Color (when blooming): Upper surface: turkey red, Red Group 46C. Under surface: cardinal red, Red Group 53B. Color (at end of opening): Upper surface: turkey red, Red Group 46B, more or less suffused with cardinal red, Red Group 53B. Under surface: cardinal red, Red Group 53B. Fragrance: none. Lasting quality: long. Petal shape: the outer petals are rounded and the inner petals are oval and sometimes possess a whitish-pink center vein. Petal number: approximately 35 to 40 on average. Texture: consistent. Petal drop: good. Stamen number: approximately 62 on average. Anthers: normal and strawlike. Filaments: strawlike, tinted with light fuschia, of irregular heights. Pistils: approximately 53 on average. Stigmas: normal and strawlike. Styles: strawlike, more or less twisted, of irregular heights. Receptacle: smooth, light green, in longitudinal section it is in the shape of a pitcher.

Development:

*Vergetation.*—very vigorous.

*Blooming.*—continuous and abundant.

*Apptitude to bear fruits.*—average.

*Resistance to frost.*—good.

*Resistance to diseases.*—very good.

I claim:

1. A new and distinct variety of Hybrid Tea rose plant characterized by the following combination of characteristics:

(a) forms continuously and in abundance attractive long lasting double blossoms which are turkey red on the upper surface and cardinal red on the under surface,
(b) exhibits an erect growth habit,
(c) exhibits very vigorous vegetation,
(d) is particularly suited for growing in parks and gardens, and
(e) is not particularly affected by cryptogamic diseases;

substantially as herein shown and described.

* * * * *

MEICAUF